(12) United States Patent
Beebe et al.

(10) Patent No.: US 10,640,530 B2
(45) Date of Patent: May 5, 2020

(54) METHOD FOR FACILITATING EXTRACTION OF A FRACTION FROM A BIOLOGICAL SAMPLE

(71) Applicant: Wisconsin Alumni Research Foundation, Madison, WI (US)

(72) Inventors: David Beebe, Monona, WI (US); Lindsay Strotman, Madison, WI (US); Scott M. Berry, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 22 days.

(21) Appl. No.: 15/891,978

(22) Filed: Feb. 8, 2018

(65) Prior Publication Data

US 2018/0162901 A1    Jun. 14, 2018

Related U.S. Application Data

(63) Continuation of application No. 13/326,832, filed on Dec. 15, 2011, now abandoned.

(51) Int. Cl.
*C07K 1/14* (2006.01)
*A61K 38/00* (2006.01)

(52) U.S. Cl.
CPC .............. *C07K 1/14* (2013.01); *C07K 1/145* (2013.01); *A61K 38/00* (2013.01)

(58) Field of Classification Search
None
See application file for complete search history.

(56) References Cited

U.S. PATENT DOCUMENTS

| | | | | |
|---|---|---|---|---|
| 5,279,936 A | * | 1/1994 | Vorpahl | C12Q 1/6813 435/5 |
| 5,691,208 A | * | 11/1997 | Miltenyi | B01D 35/06 210/695 |
| 6,117,398 A | | 9/2000 | Bienhaus et al. | |
| 7,820,454 B2 | | 10/2010 | Su et al. | |
| 8,017,340 B2 | | 9/2011 | Collier et al. | |
| 8,048,633 B2 | | 11/2011 | Collier et al. | |
| 8,304,188 B2 | | 11/2012 | Kelso et al. | |
| 8,993,243 B2 | * | 3/2015 | Beebe | G01N 33/54326 435/6.19 |
| 2004/0010235 A1 | * | 1/2004 | Weilbacher | A61M 5/31501 604/218 |
| 2004/0224380 A1 | | 11/2004 | Chou et al. | |
| 2005/0112601 A1 | | 5/2005 | Hassibi et al. | |
| 2005/0208548 A1 | | 9/2005 | Block et al. | |
| 2006/0024824 A1 | | 2/2006 | Woodside et al. | |
| 2007/0042395 A1 | | 2/2007 | Park et al. | |
| 2008/0124779 A1 | | 5/2008 | Oh et al. | |
| 2008/0226500 A1 | | 9/2008 | Shikida et al. | |
| 2009/0191594 A1 | | 7/2009 | Ohashi | |
| 2009/0246782 A1 | | 10/2009 | Kelso et al. | |
| 2010/0273142 A1 | | 10/2010 | Prins et al. | |
| 2010/0291666 A1 | | 11/2010 | Collier et al. | |
| 2012/0094275 A1 | | 4/2012 | Rao et al. | |

FOREIGN PATENT DOCUMENTS

WO    2006071770    7/2006

OTHER PUBLICATIONS

Habdas et al., "Forced motion of a probe particle near the colloidal glass transition," Europhys. Lett., 67(3), pp. 477-583, 2004.
Shikida et al., "Development of an enzymatic reaction device using magnetic bead-cluster handling," J. Micromech. Microeng. 16 (2006) 1875-1883.
Atencia et al., "Control microfludic interfaces," Nature, vol. 437, Sep. 29, 2005, 648-655.
Shikida et al., "Using wettability and interfacial tension to handle droplets of magnetic beads in a micro-chemical-analysis system," Sensors and Actuators B 133 (2006) 563-569.
Okochi et al., "Droplet-based gene expression analysis using a device with magnetic force-based-droplet-handling system," Journal of Bioscience and Bioengineering, vol. 109, No. 2, 2010, 193-197.
Tsuchiya et al., "On-chip polymerase chain reaction microdevice employing a magnetic droplet-manipulation system," Sensors and Actuators B 130 (2008) 583-588.
Maerkl et al., "A Systems Approach to Measuring the Binding Energy Landscape of Transcription Factors," Science, vol. 315, Jan. 12, 2007, 233-237.

* cited by examiner

*Primary Examiner* — Mary Maille Lyons
(74) *Attorney, Agent, or Firm* — Boyle Fredrickson, S.C.

(57) ABSTRACT

A method is provided for facilitating extraction of a fraction from a biological sample. The biological sample includes non-desired material and a fraction-bound solid phase substrate. The method includes the steps of capturing the fraction-bound solid phase substrate and bringing an isolation buffer and the fraction-bound solid phase substrate into contact to purify the captured fraction-bound solid phase substrate.

12 Claims, 6 Drawing Sheets

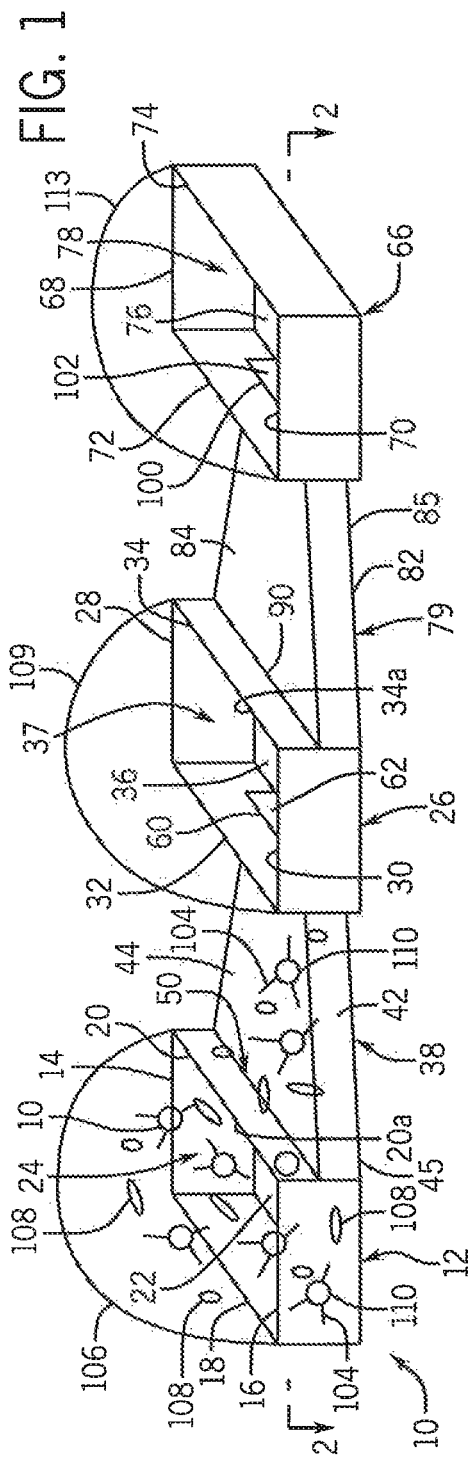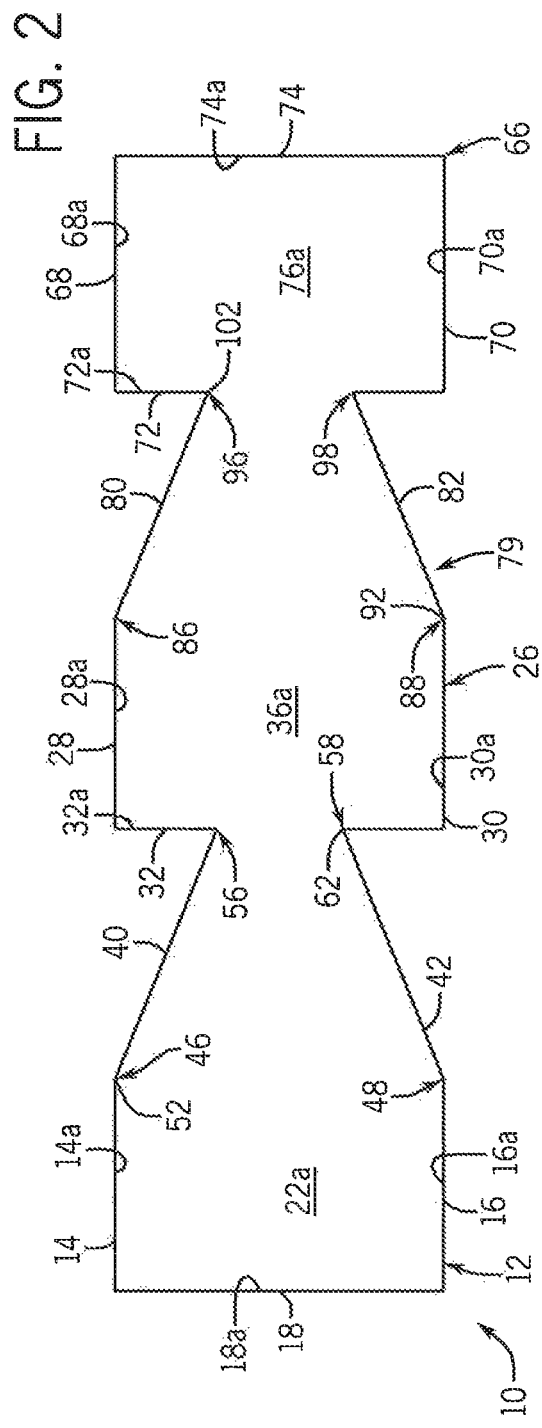

METHOD FOR FACILITATING EXTRACTION OF A FRACTION FROM A BIOLOGICAL SAMPLE

CROSS-REFERENCE TO RELATED APPLICATION

This application is a continuation of U.S. application Ser. No. 13/326,832, filed Dec. 15, 2011.

REFERENCE TO GOVERNMENT GRANT

This invention was made with government support under CA137673 awarded by the National Institutes of Health. The government has certain rights in the invention.

FIELD OF THE INVENTION

The present invention relates generally to the extraction of nucleic acid and protein purification, and in particular, to a device for and a method of extracting a fraction from cultured cells, tissue samples and other biological materials.

BACKGROUND AND SUMMARY OF THE INVENTION

Effective isolation of nucleic acids from biological samples (e.g. cultured cells, tissue, viruses) is an essential prerequisite for efficient downstream amplification, detection, and quantification of specific genetic sequences via quantitative polymerase chain reaction (qPCR). The extraction process requires lysing the cells with harsh extraction reagents, such as detergents or enzymes, thereby resulting in a mixture of nucleic acids, cellular debris and extraction reagents. The nucleic acids are then separated/purified from the cellular debris and extraction reagents using a variety of techniques (e.g. organic solvent extraction, chromatography, centrifugation, dialysis). These techniques can be very time-consuming, tedious, and often require multiple washing steps. By way of example, commercially-available nucleic acid isolation kits require approximately 15 minutes to over one hour to complete, largely due to the multiple washing steps required to sufficiently separate the nucleic acids from the cellular debris and extraction reagents. Consequently, it has been suggested that as much as 15% of all molecular biology research time is devoted to purification.

In view of the foregoing, various attempts have been made to reduce the time associated with isolating nucleic acids from a biological sample. By way of example, Kelso, United States Patent Application No. 20090246782 discloses a system, device, and method for performing biological reactions. More specifically, the system contemplates placing a sample in a first chamber. The first chamber includes first processing reagents to generate a processed sample. The processed sample is moved through a water and alcohol immiscible, hydrophobic, or lipophilic barrier to a second chamber. The processed sample is treated in said second chamber with second processing reagents to generate a further processed sample.

While functional for its intended purpose, the system disclosed in the '782 application has certain limitations. For example, the reagents and immiscible phase of the system disclosed in the '782 application must be confined within corresponding chambers. As a result, the system requires the use of an external pump or two-axis magnet to move the processed sample between the chambers. It can be appreciated that the use of an external pump may have undesired effects on the sample. Alternatively, the use of a two-axis magnet may add unwanted cost and complexity to the system. In addition, the use of a plurality of chambers to isolate the nucleic acids from a biological sample may limit the throughput of the system.

Therefore, it is a primary object and feature of the present invention to provide a method of extracting and purifying a fraction from cultured cells, tissue samples and other biological materials.

It is a further object and feature of the present invention to provide a method of extracting and purifying a fraction from cultured cells, tissue samples and other biological materials that is simpler and more efficient than prior methods.

It is a still further object and feature of the present invention to provide a method of extracting and purifying a fraction from cultured cells, tissue samples and other biological materials that has higher throughput than prior methods.

In accordance with the present invention, a method is provided for facilitating extraction of a fraction from a biological sample. The biological sample includes non-desired material and a fraction-bound solid phase substrate. The method includes the steps of capturing the fraction-bound solid phase substrate and bringing an isolation buffer and the fraction-bound solid phase substrate into contact to purify the captured fraction-bound solid phase substrate.

The method may also include the step of sequentially drawing the isolation buffer and the biological sample into a barrel of a syringe. The step of bringing the isolation buffer and the fraction-bound solid phase substrate into contact includes the step of sequentially urging the biological sample and the isolation buffer from the barrel of the syringe. Alternatively, the step of bringing an isolation buffer and the fraction-bound solid phase substrate into contact may include the additional steps adhering the isolation buffer to a surface and bringing the surface into contact with the fraction-bound solid phase substrate. In order to bring the surface into contact with the fraction-bound solid phase substrate, the surface may be slid across the fraction-bound solid phase substrate.

Further, it is contemplated to position the captured fraction-bound solid phase substrate in an air channel prior to the step of bringing the isolation buffer and the fraction-bound solid phase substrate into contact. In order to position the captured fraction-bound solid phase substrate in the air channel, the biological sample may be allowed to evaporate. Alternatively, the captured fraction-bound solid phase substrate fraction may be drawn into the air channel with a magnetic force.

In accordance with a further aspect of the present invention, a method is provided for facilitating extraction of a fraction from a biological sample. The biological sample including non-desired material and a fraction-bound solid phase substrate. The method includes the step of capturing the fraction-bound solid phase substrate with a magnetic force. The captured fraction-bound solid phase substrate is purified with an isolation buffer.

The method may include the additional step of sequentially drawing the isolation buffer and the biological sample into a barrel of a syringe prior to capturing the fraction-bound solid phase substrate. The captured fraction-bound solid phase substrate is purified by sequentially urging the biological sample and the isolation buffer from the barrel of the syringe. Alternatively, the captured fraction-bound solid phase substrate may be purified by adhering the isolation buffer to a surface and bringing the surface into contact with the fraction-bound solid phase substrate. For example, the surface may be slid across the fraction-bound solid phase substrate.

The captured fraction-bound solid phase substrate may be positioned in an air channel prior to the step of purifying the captured fraction-bound solid phase substrate fraction. The captured fraction-bound solid phase substrate may be positioned in the air channel by allowing the biological sample to evaporate. Alternatively, the captured fraction-bound solid phase substrate may be drawn into the air channel with a magnetic force.

In accordance with a still aspect of the present invention, a method is provided for facilitating extraction of a fraction from a biological sample. The biological sample includes non-desired material and a fraction-bound solid phase substrate. The method includes the steps of capturing the fraction-bound solid phase substrate with a magnetic force and moving an isolation buffer into contact with the captured fraction-bound solid phase substrate.

The method may include the additional step of sequentially drawing the isolation buffer and the biological sample into a barrel of a syringe prior to capturing the fraction-bound solid phase substrate. The isolation buffer may be moved by sequentially urging the biological sample and the isolation buffer from the barrel of the syringe. Alternatively, the isolation buffer may be moved by adhering the isolation buffer to a surface and bringing the surface into contact with the fraction-bound solid phase substrate. By way of example, the surface may be slid across the fraction-bound solid phase substrate.

Prior to moving the isolation buffer into contact with the fraction-bound solid phase substrate, the captured fraction-bound solid phase substrate may be positioned in an air. In order to position the captured fraction-bound solid phase substrate in the air channel, the biological sample may be allowed to evaporate. Alternatively, the captured fraction-bound solid phase substrate fraction may be drawn into the air channel with a magnetic force.

BRIEF DESCRIPTION OF THE DRAWINGS

The drawings furnished herewith illustrate a preferred construction of the present invention in which the above advantages and features are clearly disclosed as well as others which will be readily understood from the following description of the illustrated embodiment.

In the drawings:

FIG. 1 is an isometric view of a device for effectuating a methodology in accordance with the present invention in an initial configuration;

FIG. 2 is a cross-sectional view of the device taken along line 2-2 of FIG. 1;

DETAILED DESCRIPTION OF THE DRAWINGS

Figure 3:
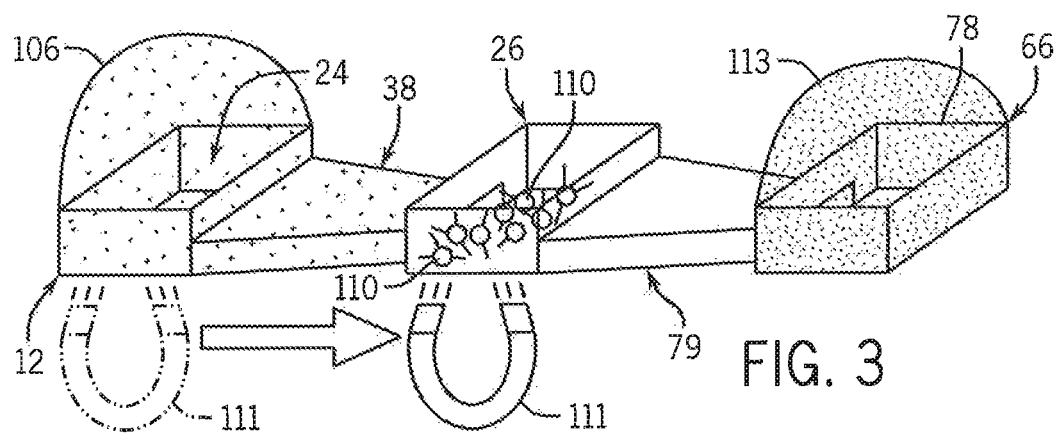
FIG. 3 is an isometric view of the device of FIG. 1 in a second configuration.
Figure 4:
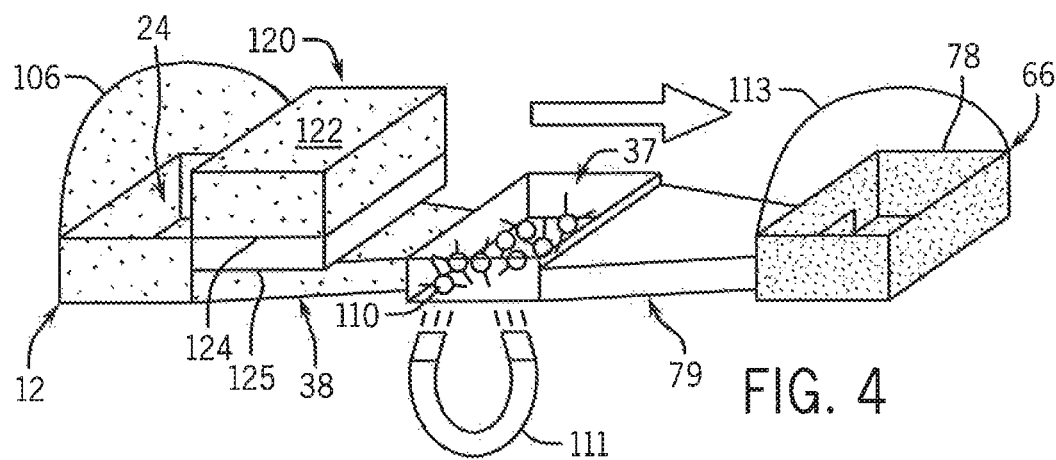
FIG. 4 is an isometric view of the device of FIG. 1 in a third configuration.
Figure 5:
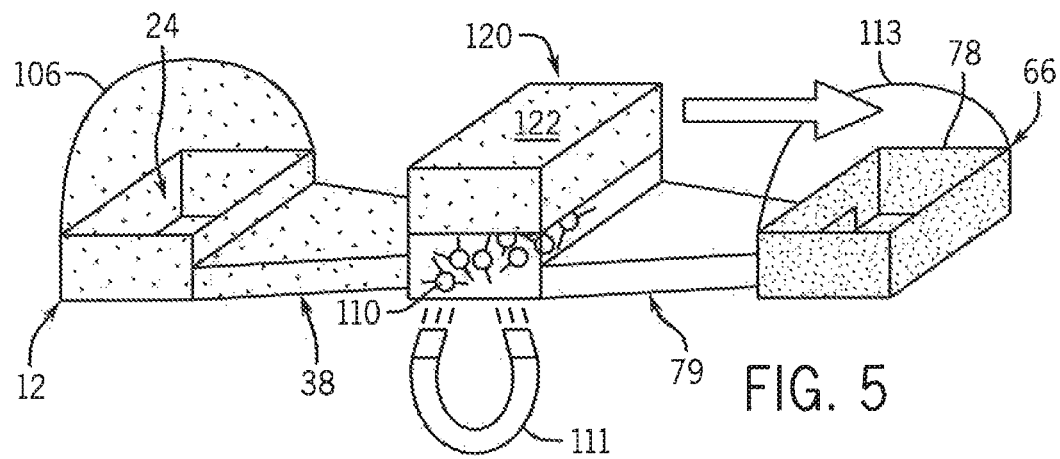
FIG. 5 is an isometric view of the device of FIG. 1 in a fourth configuration.
Figure 6:
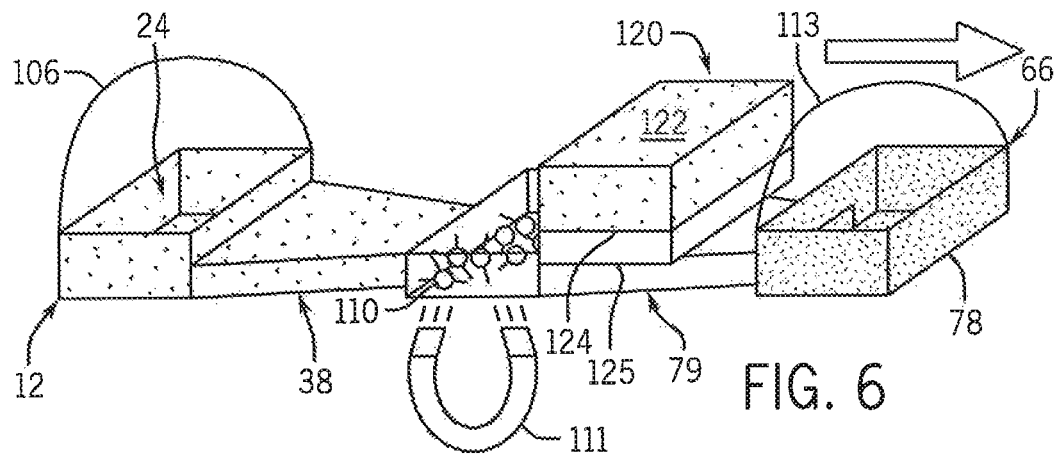
FIG. 6 is an isometric view of the device of FIG. 1 in a fifth configuration.

Referring to FIGS. 1-3, a device for extracting and purifying a fraction from cultured cells, tissue samples and other biological materials in accordance with the present invention is generally designated by the reference numeral 10. Device 10 includes input zone or well 12 defined by first and second sidewalls 14 and 16, respectively, first and second end walls 18 and 20, respectively, and bottom wall 22. Inner surfaces 14a and 16a of sidewalls 14 and 16, respectively, inner surfaces 18a and 20a of first and second end walls 18 and 20, respectively, and upper surface 22a of bottom wall 22 define input cavity 24 for receiving a biological sample therein, as hereinafter described. While input well 12 has a generally rectangular configuration in the depicted embodiment, other configurations are contemplated without deviating from the scope of the present invention.

Device 10 further includes isolation well 26 being defined by first and second sidewalls 28 and 30, respectively, upstream wall 32, downstream wall 34 and bottom wall 36. Inner surfaces 28a and 30a of sidewalls 28 and 30, respectively, inner surface 32a of upstream wall 32, inner surface 34a of downstream wall 34, and upper surface 36a of bottom wall 36 define an air channel, e.g. isolation cavity 37, for reasons hereinafter described. Again, although isolation well 26 has a generally rectangular configuration in the depicted embodiment, other configurations are contemplated without deviating from the scope of the present invention.

Input well 12 and isolation well 26 are interconnected by first channel 38. First channel 38 extends along an axis and is defined by first and second sidewalls 40 and 42, respectively, upper wall 44 and bottom wall 45. Input ends 46 and 48 of first and second sidewalls 40 and 42, respectively, of first channel 38 and input end 50 of upper wall 44 of input channel 38 intersect end wall 20 of input well 12 so as to define input 52 to first channel 38. Output ends 56 and 58 of first and second sidewalls 40 and 42, respectively, of first channel 38 and output end 60 of upper wall 44 of first channel 38 intersect upstream wall 32 of isolation well 26 so as to define output 62 of first channel 38. Bottom wall 45 of first channel 38 is generally co-planar with bottom walls 22 and 36 of input well 12 and isolation well 26, respectively. As best seen in FIG. 2, first and second sidewalls 40 and 42, respectively, of first channel 38 converge towards each other from input 52 to output 62.

Device 10 further includes output zone or well 66 downstream of isolation well 26 and being defined by first and second sidewalls 68 and 70, respectively, upstream wall 72, downstream wall 74 and bottom wall 76. Inner surfaces 68a and 70a of sidewalls 68 and 70, respectively, inner surface 72a of upstream wall 72, inner surface 74a of downstream wall 74, and upper surface 76a of bottom wall 76 define output cavity 78 for receiving a reagent therein, as hereinafter described. Again, output well 66 has a generally rectangular configuration in the depicted embodiment, other configurations are contemplated without deviating from the scope of the present invention.

Output well 66 and isolation well 26 are interconnected by second channel 79. Second channel 79 extends along an axis and is defined by first and second sidewalls 80 and 82, respectively, upper wall 84 and bottom wall 85. Input ends 86 and 88 of first and second sidewalls 80 and 82, respectively, of second channel 79 and input end 90 of upper wall 84 of second channel 79 intersect downstream wall 34 of isolation well 26 so as to define input 92 to second channel 79. Output ends 96 and 98 of first and second sidewalls 80 and 82, respectively, of second channel 79 and output end 100 of upper wall 84 of second channel 79 intersect upstream wall 72 of output well 66 so as to define output 102 of second channel 79. Bottom wall 76 of second channel 79 is generally co-planar with bottom walls 36 and 76 of isolation well 26 and output well 66, respectively. As best seen in FIG. 2, first and second sidewalls 80 and 82, respectively, of second channel 79 converge towards each other from input 92 to output 102.

Referring to FIGS. 3-6, device 10 further includes stamp 120 having a generally square configuration and being partially defined by upper surface 122 and lower surface 124. It is contemplated for the dimensions of stamp 120 to approximate the dimensions of isolation cavity 37 in isolation well 26. Further, it is contemplated for lower surface 124 to have a high affinity for adhering an isolation buffer 125, such as oil, thereto. It is noted that while stamp 120 has a generally rectangular configuration in the depicted embodiment, other configurations are contemplated without deviating from the scope of the present invention.

In operation, it is intended to utilize device 10 to extract fraction 104, such as analytes, nucleic acids, whole cells and/or proteins, from biological sample 106. As is known, biological sample 106 may include non-desired material 108 such as lysate, bodily fluids, forensic samples, and/or biological contaminations. In order to prepare biological sample 106 for extraction of fraction 104, an appropriate reagent is added to biological sample 106 and mixed such that fraction 104 binds to a solid phase substrate in the reagent to form fraction-bound solid phase substrate 110. It is contemplated for the solid phase substrate to be attracted to a corresponding force. For example, the solid phase substrate may be a paramagnetic material attracted to a corresponding magnetic field. Other non-magnetic mechanisms such as gravity, ultrasonic actuation or the like are contemplated as being within the scope of the present invention. Once mixed with the reagent, biological sample 106 is deposited in input cavity 24 of input well 12; and a desired reagent, such as elution buffer 113, is deposited in output cavity 78 of output well 66. It can be appreciated that the mixing of biological sample 106 and the reagent may occur in input cavity 24 of input well 12 and/or first channel 38 without deviating from the scope of the present invention.

It is noted that the cross-sectional area of input 52 to first channel 38 is greater than the cross-sectional area of output 62 of first channel 38. As a result, biological sample 106 flows into first channel 38 through input 52 thereof. However, the surface tension at the interface of biological sample 106 and the air in isolation cavity 37 of isolation well 26 at output 62 of first channel 38 prevents biological sample 106 from flowing into isolation cavity 37 of isolation well 26 through output 62 of first channel 38. Likewise, the surface tension between the air at output 102 of second channel 79 and elution buffer 113 in output cavity 78 of output well 66 at output 102 of second channel 79 prevents elution buffer 113 from flowing into second channel 79 through output 102 thereof.

In order to extract fraction-bound solid phase substrate 110 from biological sample 106, a force to which the solid phase substrate is attracted is positioned adjacent, and preferably below, input well 12. As heretofore described, it is contemplated for the solid phase substrate to be a paramagnetic material attracted to a corresponding magnetic field. As such, in order to generate the magnetic field, magnet 111 is positioned below input well 12 such that fraction-bound solid phase substrate 110 is magnetically attracted thereto. Magnet 111 is sequentially moved from a position below bottom wall 45 of first channel 38 such that fraction-bound solid phase substrate 110 are drawn into first channel 38 through input 52 thereof to a position below bottom wall 36 of isolation well 26 such that fraction-bound solid phase substrate 110 are drawn into isolation well 26 through output 62 of first channel 38.

Figure 13:
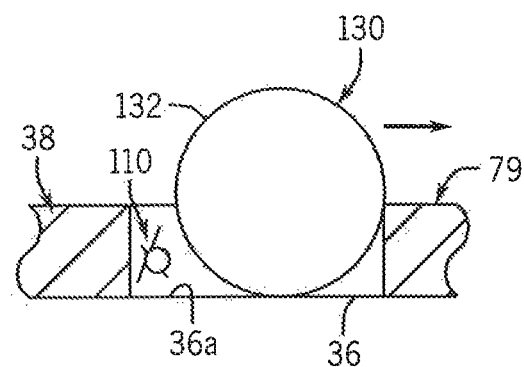
FIG. 13 is an alternate embodiment of a stamp for the device for effectuating a methodology in accordance with the present invention.

With fraction-bound solid phase substrate 110 drawn into isolation cavity 37 of isolation well 26, it is contemplated to slide lower surface 124 of stamp 120 across upper surface 36a of bottom wall 36. More specifically, stamp 120 is positioned above first channel, FIG. 4, and slid axially toward output well 66 such that lower surface 124 of stamp 120 slides across upper surface 36a of bottom wall 36 of isolation well 26, FIG. 5. As the lower surface 124 of stamp 120 slides across upper surface 36a of bottom wall 36 of isolation well 26, isolation buffer 125 adhered to lower surface 124 of stamp 120 captures any non-desired material 108 such as lysate, bodily fluids, forensic samples, and/or biological contaminations carried by fraction-bound solid phase substrate 110, thereby effectively washing fraction-bound solid phase substrate 110 with isolation buffer 125. It can be appreciated that upon disengagement of lower surface 124 of stamp 120 from upper surface 36a of bottom wall 36, FIG. 6, fraction-bound solid phase substrate 110 retained in isolation cavity 37 by magnet 111 is isolated from the non-desired material 108 of biological sample 106. Alternatively, it is contemplated for the generally rectangular configuration of stamp 120 to be replaced with a roller-like stamp 130 having such that a radially outer surface 132 with a high affinity for adhering isolation buffer, such as oil, thereto, FIG. 13. The configuration of stamp 130 allows for outer surface 132 of stamp 130 to be simply and easily rolled over upper surface 36a of bottom wall 36 to capture any non-desired material 108 such as lysate, bodily fluids, forensic samples, and/or biological contaminations, carried by fraction-bound solid phase substrate 110.

Figure 7:
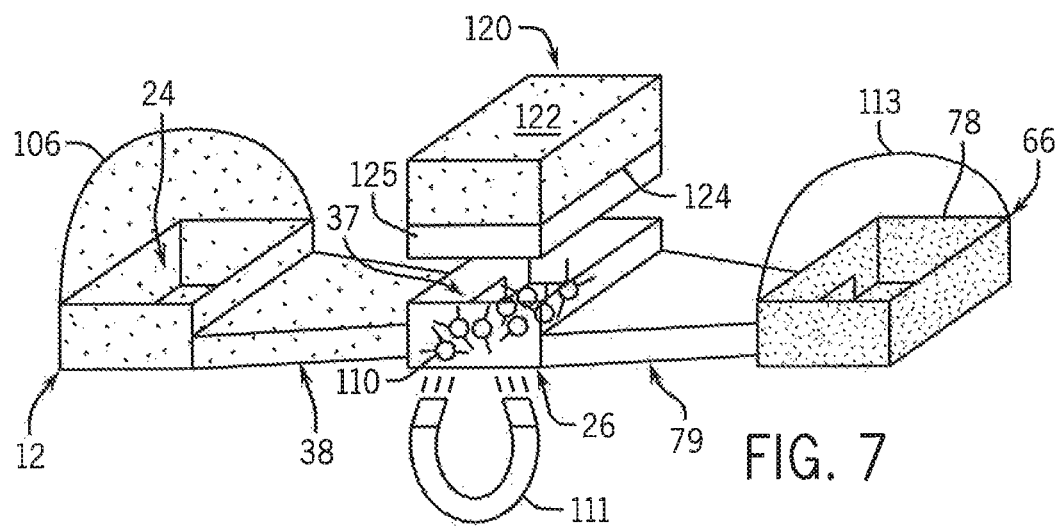
FIG. 7 is an isometric view of an alternate embodiment of the device for effectuating a methodology in accordance with the present invention in an initial configuration.
Figure 8:
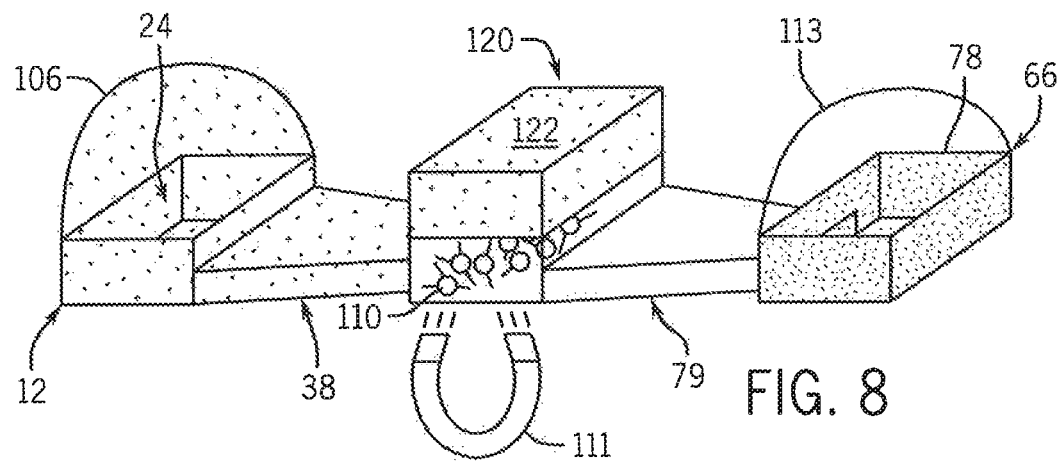
FIG. 8 is an isometric view of the device of FIG. 7 in a second configuration.
Figure 9:
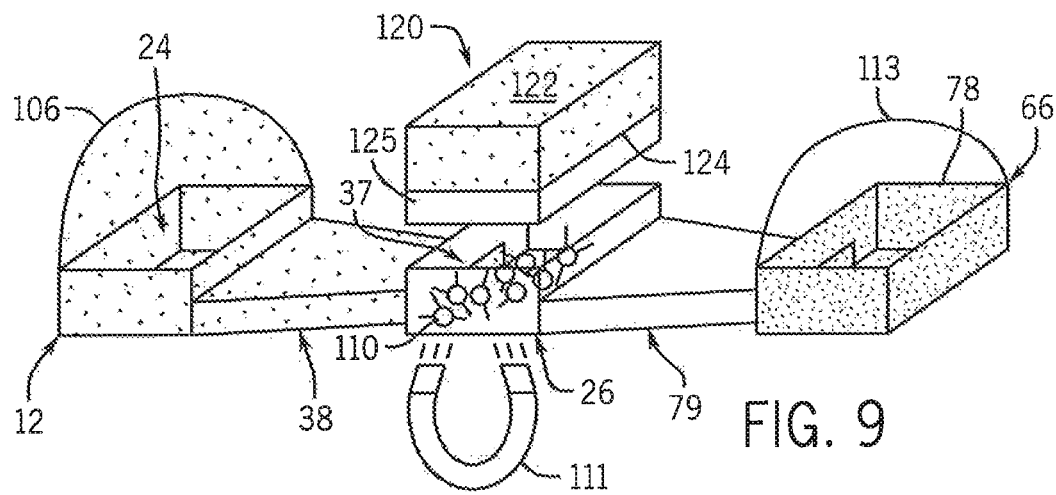
FIG. 9 is an isometric view of the device of FIG. 7 in a third configuration.

In an alternate methodology, FIGS. 7-9, stamp 120 is positioned such that lower surface 124 thereof is axially aligned with isolation cavity 37, FIG. 7. Stamp 120 is lowered such that lower surface 124 is brought into contact with upper surface 36a of bottom wall 36, FIG. 8. As lower surface 124 of stamp 120 is brought into contact with upper surface 36a of bottom wall 36, the isolation buffer adhered to lower surface 124 of stamp 120 captures any non-desired material 108 such as lysate, bodily fluids, forensic samples, and/or biological contaminations, carried by fraction-bound solid phase substrate 110, thereby effectively washing fraction-bound solid phase substrate 110 with the isolation buffer. Thereafter, stamp 120 is raised such that lower surface 124 containing the captured non-desired material 108 is spaced from upper surface 36a of bottom wall 36 so as to isolate fraction-bound solid phase substrate 110 retained in isolation cavity 37 by magnet 111 from the non-desired material 108, FIG. 9.

Once fraction-bound solid phase substrate 110 is isolated from the non-desired material 108 of biological sample 106, as heretofore described, magnet 111 is sequentially moved from a position below bottom wall 36 of isolation well 26 to: 1) a position below bottom wall 85 of second channel 79 such that fraction-bound solid phase substrate 110 are drawn into second channel 79 through input 92 thereof; and 2) below bottom wall 76 of output well 66 such that fraction-bound solid phase substrate 110 are drawn into output well 66 through output 102 of second channel 79. With fraction-bound solid phase substrate 110 in output well 66, fraction-bound solid phase substrate 110 may be treated in output well 66 by elution buffer 113 contained therein, as desired by a user. It is also contemplated to fill output well 66 with an additional isolation buffer or aqueous buffer for further washing of fraction-bound solid phase substrate 110. In addition, it can be appreciated that output well 66 may be operatively connected to additional downstream components for further processing of fraction-bound solid phase substrate 110.

As described, the methodology of the present invention does not require any electronic equipment such as centrifuges, rockers/shakers, or incubators, while consuming only minimal volumes of reagents in the two wells. It can also be appreciated that the simplicity of device 10 allows for it to be easily reconfigured to form a mating relationship with the input/output requirements of upstream and downstream components.

Figure 10A:
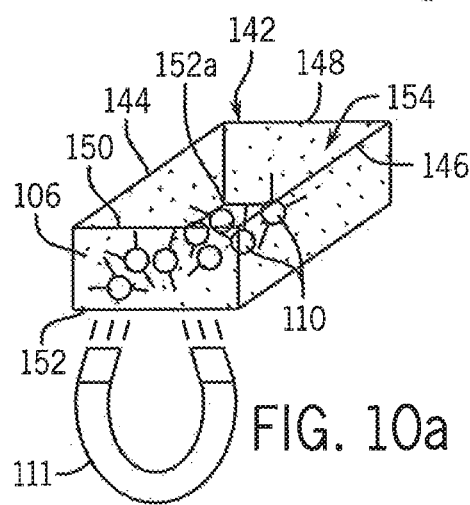
FIG. 10a is an isometric view of a further alternate embodiment of the device for effectuating a methodology in accordance with the present invention in an initial configuration.
Figure 10B:
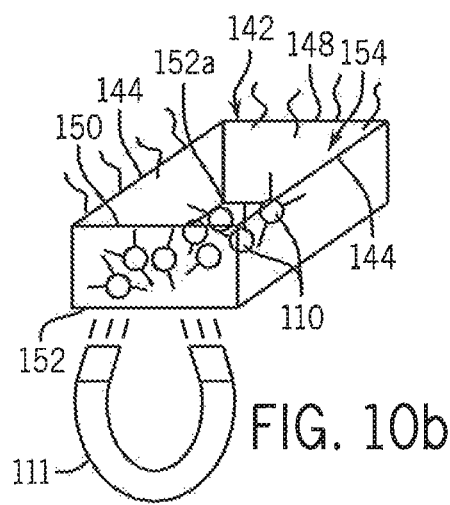
FIG. 10b is an isometric view of the device of FIG. 10a in a second configuration.

Alternatively, referring to FIGS. 10a-10b, in order to extract fraction-bound solid phase substrate 110 from biological sample 106, it is contemplated to provide a single input well 142 defined by first and second sidewalls 144 and 146, respectively, first and second end walls 148 and 150, respectively, and bottom wall 152. The inner surfaces of sidewalls 144 and 146, respectively, the inner surfaces of first and second end walls 148 and 150, respectively, and upper surface 152a of bottom wall 152 define input cavity 154 for receiving biological sample 106 therein. It is noted while input well 142 has a generally rectangular configuration in the depicted embodiment, other configurations are contemplated without deviating from the scope of the present invention.

In operation, biological sample 106 having a desired fraction 104 is mixed with reagent having a solid phase substrate such that fraction 104 in biological sample 106 binds to the solid phase substrate in the reagent to form fraction-bound solid phase substrate 110. It is contemplated for the solid phase substrate to be attracted to a corresponding force. For example, the solid phase substrate may be a paramagnetic material attracted to a corresponding magnetic field. Other non-magnetic mechanisms such as gravity, ultrasonic actuation or the like are contemplated as being within the scope of the present invention. Once mixed with the reagent, biological sample 106 is deposited in input cavity 154 of input well 142, FIG. 10a.

With biological sample 106 deposited in input cavity 154 of input well 142, it is contemplated for a user to allow biological sample 106 to evaporate, FIG. 10b. Thereafter, magnet 111 is positioned below input well 142 such that fraction-bound solid phase substrate 110 is magnetically attracted thereto. Stamp 120 is positioned such that lower surface 124 having an isolation buffer adhered thereto is axially aligned with input cavity 154. Stamp 120 is lowered such that lower surface 124 is brought into contact with upper surface 152a of bottom wall 152. As lower surface 124 of stamp 120 is brought into contact with upper surface 152a of bottom wall 152, isolation buffer 125 adhered to lower surface 124 of stamp 120 captures any non-desired material 108 such as lysate, bodily fluids, forensic samples, and/or biological contaminations, carried by fraction-bound solid phase substrate 110, thereby effectively washing fraction-bound solid phase substrate 110 with isolation buffer 125. Magnet 111 retains fraction-bound solid phase substrate 110 within input well 142 as stamp 120 is raised such that lower surface 124 containing the captured non-desired material 108 is spaced from upper surface 152a of bottom wall 152, thereby isolating fraction-bound solid phase substrate 110 from the non-desired material 108 of biological sample 106. The fraction-bound solid phase substrate 110 is now ready for further processing. Alternatively, it can be appreciated that fraction-bound solid phase substrate 110 may be isolated from non-desired material 108 of biological sample 106 by sliding slide lower surface 124 of stamp 120 across upper surface 152a of bottom wall 152 or by rolling outer surface 132 of stamp 130 over upper surface 152a of bottom wall 152, as heretofore described.

Figure 11A:
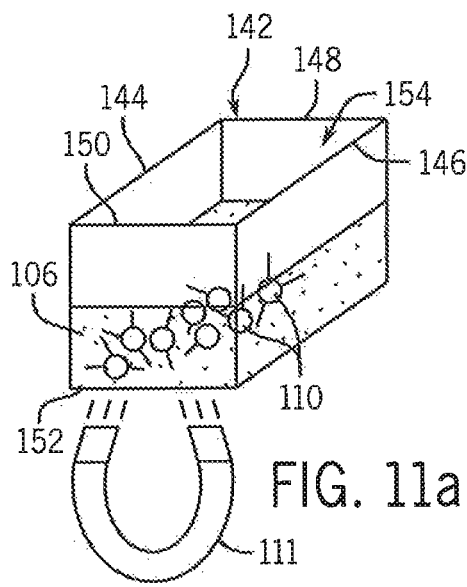
FIG. 11a is an isometric view of a still further alternate embodiment of the device for effectuating a methodology in accordance with the present invention in an initial configuration.
Figure 11B:
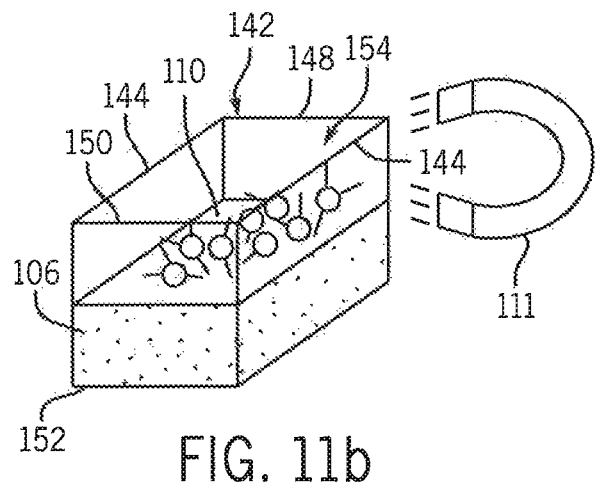
FIG. 11b is an isometric view of the device of FIG. 11a in a second configuration.

As best seen in FIGS. 11a-11b, instead of allowing biological sample 106 in input well 142 to evaporate, it is contemplated to remove fraction-bound solid phase substrate 110 from biological sample 106 by means of magnet 111. More specifically, in operation, magnet 111 is positioned below input well 142 such that fraction-bound solid phase substrate 110 is magnetically attracted thereto, FIG. 11a. Magnet 111 is moved to a second position, FIG. 11b, such that fraction-bound solid phase substrate 110 is elevated above biological sample 106 in input well 142. With fraction-bound solid phase substrate 110 elevated above biological sample 106, stamp 120 is aligned with fraction-bound solid phase substrate 110 and brought into contact therewith such that isolation buffer 125 adhered to lower surface 124 of stamp 120 captures any non-desired material 108 such as lysate, bodily fluids, forensic samples, and/or biological contaminations, carried by fraction-bound solid phase substrate 110. As such, fraction-bound solid phase substrate 110 is effectively washed with isolation buffer 125. Magnet 111 retains fraction-bound solid phase substrate 110 in input well 142 as stamp 120 disengages from fraction-bound solid phase substrate 110, thereby isolating fraction-bound solid phase substrate 110 from the non-desired material 108 of biological sample 106. The fraction-bound solid phase substrate 110 is now ready for further processing.

Referring to FIGS. 12a-12f, an alternate embodiment of the device for extracting and purifying a fraction from cultured cells, tissue samples and other biological materials in accordance with the present invention is generally designated by the reference numeral 160. Device 160 may take the form of a syringe having a generally hollow barrel 162. Barrel includes inner surface 163 defining passageway 165 therethrough and an outer surface 167. Barrel 162 further includes a first end 164 terminating at opening 166 and a second end 168 terminating at opening 170. In the depicted embodiment, first end 164 is generally conical and opening 166 in first end 164 is substantially smaller than opening 170 in second end 168. However, other configurations of barrel 162 are possible without deviating from the scope of the present invention. For example, the barrel 162 may take the form of a tube or a conduit having a non-circular cross-section. Further, opening 166 in first end 164 of barrel 162 need not be substantially smaller than opening 170 in second end 168. Preferably, it is contemplated for opening 166 to have a diameter less than 3 millimeters. However, other diameters of opening 166 are possible with deviating from the scope of the present invention.

Device 160 further includes plunger 172 partially received in passageway 165 through barrel 162. Plunger 172 includes an elongated stem 174 having first and second opposite ends 176 and 178, respectively. Resilient plunger head 180 extends radially from first end 176 of stem 174 and terminates at a radially outer edge 182. Outer edge 182 slidably engages inner surface 163 of barrel 162 and forms an airtight seal therewith. It can be appreciated that plunger head 180 divides passageway 165 into first and second chambers 184 and 186, respectively, the volumes of which vary depending on the position of plunger head 180 along inner surface 163 of barrel 162. Second end 178 of stem 174 includes thumb rest 188 projecting radially therefrom. Thumb rest 188 has an outer surface 190 adapted for receiving a thumb of an individual using device 160 so as to facilitate the reciprocal movement of plunger head 180, as hereinafter described.

Figure 12A:
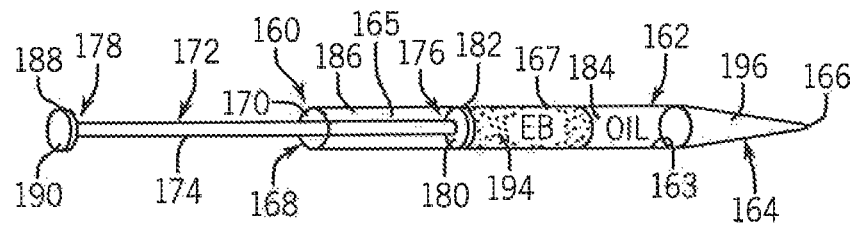
FIG. 12a is a schematic view of a still further alternate embodiment of the device for effectuating a methodology in accordance with the present invention in a first configuration.
Figure 12B:
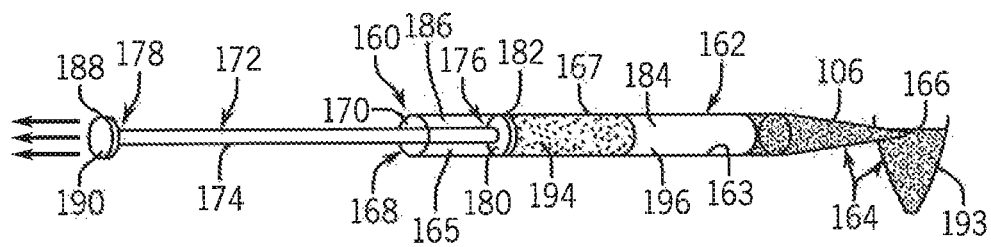
FIG. 12b is an schematic view of the device of FIG. 12a in a second configuration.
Figure 12C:
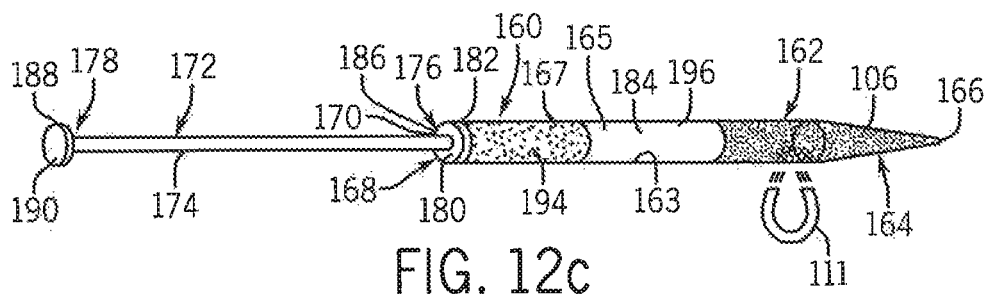
FIG. 12c is an schematic view of the device of FIG. 12a in a third configuration.
Figure 12D:
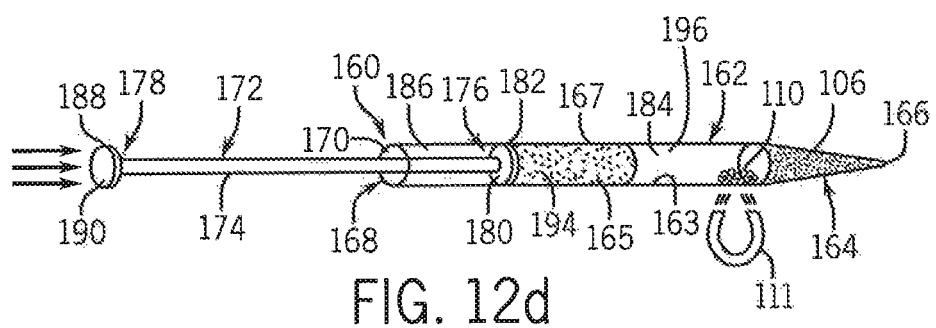
FIG. 12d is an schematic view of the device of FIG. 12a in a fourth configuration.

In order to prepare biological sample 106 for extraction of fraction 104, an appropriate reagent is added to biological sample 106 in vessel 193, FIG. 12b, and mixed such that fraction 104 binds to a solid phase substrate in the reagent to form fraction-bound solid phase substrate 110. It is contemplated for the solid phase substrate to be attracted to a corresponding force. For example, the solid phase substrate may be a paramagnetic material attracted to a corresponding magnetic field. Other non-magnetic mechanisms such as gravity, ultrasonic actuation or the like are contemplated as being within the scope of the present invention.

Plunger 172 is inserted fully into barrel 162 such that plunger head 180 abuts first end first end 164 of barrel 162. Thereafter, opening 166 in first end 164 of barrel 162 is inserted into a supply of reagent, such as elution buffer 194, and plunger 172 is retracted so as to draw a volume of elution buffer 194 into first chamber 184 of passageway 165 of barrel 162 through opening 166, FIG. 12a. Opening 166 in first end 164 of barrel 162 is then removed from the supply of the elution buffer 194 and inserted into a supply of isolation buffer 196, such as oil. Plunger 172 is further retracted so as to draw a volume of isolation buffer 196 into first chamber 184 of passageway 165 of barrel 162 through opening 166, FIG. 12a. Opening 166 in first end 164 of barrel 162 is then removed from the supply of isolation buffer 196 and inserted into vessel 193, FIG. 12b. Plunger 172 is further retracted so as to draw a volume of biological sample 106 into first chamber 184 of passageway 165 of barrel 162 through opening 166, FIG. 12c.

In order to extract fraction-bound solid phase substrate 110 from biological sample 106, a force to which the solid phase substrate is attracted is positioned adjacent, and preferably adjacent the volume of biological sample 106 in first chamber 184 of passageway 165 of barrel 162. As heretofore described, it is contemplated for the solid phase substrate to be a paramagnetic material attracted to a corresponding magnetic field. As such, in order to generate the magnetic field, magnet 111 is positioned adjacent barrel 162 at a location adjacent the volume of biological sample 106 in first chamber 184 thereof such that fraction-bound solid phase substrate 110 is magnetically attracted thereto, FIG. 12c. Thereafter, plunger 172 is fully inserted back into barrel 162 so as to sequentially urge: 1) biological sample 106 out of first chamber 184 of passageway 165 of barrel 162 through opening 166, FIG. 12d; and 2) isolation buffer 196 out of first chamber 184 of passageway 165 of barrel 162 through opening 166, FIG. 12e. It can be appreciated that as plunger 172 is inserted back into barrel 162, magnet 111 retains fraction-bound solid phase substrate 110 in first chamber 184. Further, it can be appreciated that as isolation buffer 196 passes over the magnetically retained fraction-bound solid phase substrate 110 in first chamber 184, isolation buffer 196 captures any non-desired material 108 such as lysate, bodily fluids, forensic samples, and/or biological contaminations, carried by fraction-bound solid phase substrate 110, thereby effectively washing fraction-bound solid phase substrate 110.

Figure 12E:
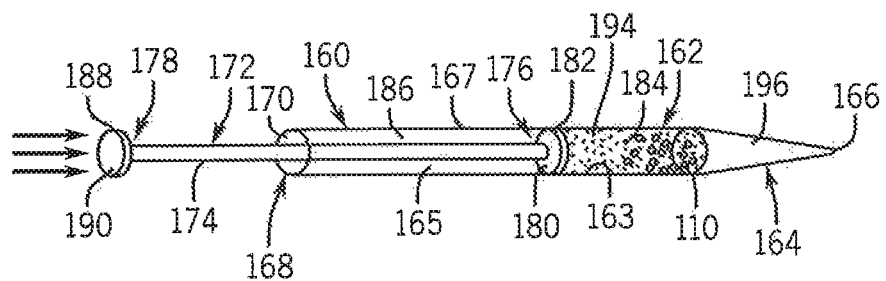
FIG. 12e is an schematic view of the device of FIG. 12a in a fifth configuration.
Figure 12F:
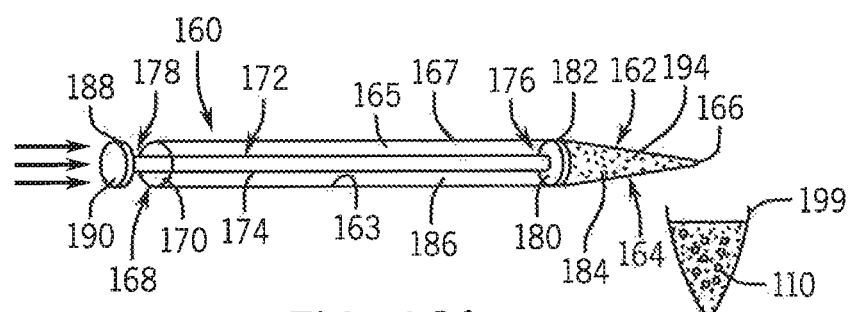
FIG. 12f is an schematic view of the device of FIG. 12a in a sixth configuration.

Once elution buffer 194 comes into contact with fraction-bound solid phase substrate 110 in first chamber 184, magnet 111 is removed, FIG. 12e. As plunger 172 is fully inserted back into barrel 162, FIG. 12f, elution buffer 194 carries fraction-bound solid phase substrate 110 out of first chamber 184 of passageway 165 of barrel 162 through opening 166 and into vessel 199. Thereafter, vessel 199 may be operatively connected to additional downstream components for further processing of the purified fraction-bound solid phase substrate 110. It can also be appreciated that additional isolation buffers or aqueous buffers may be provided between isolation buffer 196 and elution buffer 194 in barrel 162 for further washing of fraction-bound solid phase substrate 110, in a manner heretofore described.

Various modes of carrying out the invention are contemplated as being within the scope of the following claims particularly pointing out and distinctly claiming the subject matter, which is regarded as the invention.

We claim:

1. A method for facilitating extraction of a fraction from a biological sample, the biological sample including non-desired material and a fraction-bound solid phase substrate, the method comprising the steps of:
    positioning at least a portion of a plunger within a passageway extending along axis through a barrel of a syringe, the plunger being slidable along the axis and including:
        an elongated stem having a first end received in the barrel; and
        a resilient plunger head extending radially from first end of the stem and terminating at a radially outer edge, the radially outer edge of the plunger head forming an airtight seal with an inner surface of the barrel;
    sliding the plunger along the axis of the barrel in a first direction such that the plunger head is positioned adjacent an opening in a first end of barrel;
    positioning the opening in the first end of the barrel in fluid communication with an isolation buffer;
    sliding the plunger along the axis of the barrel in a second direction, opposite to the first direction, for a first user-selected distance so as to draw the isolation buffer into the passageway in the barrel through the opening;

positioning the opening in the first end of the barrel in fluid communication with the biological sample;

sliding the plunger along the axis of the barrel in a second direction for a second user-selected distance so as to draw the biological sample into the passageway in the barrel through the opening;

positioning a magnet adjacent to an outer surface of the barrel in proximity to the first end of the barrel such that a magnetic field generated by the magnet captures the fraction-bound solid phase substrate at a fixed location within the passageway through the barrel of the syringe;

sliding the plunger along the axis of the barrel in the first direction so as to urge the biological sample from the passageway in the barrel through the opening while maintaining the captured fraction-bound solid phase substrate at the fixed location;

sliding the plunger along the axis of the barrel in the first direction such that at least a portion of the isolation buffer contacts the captured fraction-bound solid phase substrate at the fixed location and flows out of the passageway in the barrel through the opening;

removing the magnet from adjacent to an outer surface of the barrel such that the fraction-bound solid phase substrate is no longer captured at the fixed location within the passageway through the barrel of the syringe; and sliding the plunger along the axis of the barrel in the first direction such that the fraction-bound solid phase substrate is urged from the passageway in the barrel through the opening;

wherein:

the isolation buffer and the biological sample are immiscible; and prior to the step of positioning the opening in the first end of the barrel in fluid communication with the isolation buffer including the additional steps of:

positioning the opening in the first end of the barrel in fluid communication with an elusion buffer; and sliding the plunger along the axis of the barrel in the second direction for a third user-selected distance so as to draw the elusion buffer into the passageway in the barrel through the opening.

2. The method of claim 1 wherein prior to the step of removing the magnet from adjacent to the outer surface of the barrel, comprising the additional step of sliding the plunger along the axis of the barrel in the first direction such that at least a portion of the elusion buffer contacts the captured fraction-bound solid phase substrate at the fixed location.

3. The method of claim 1 wherein the elusion buffer is urged from the passageway in the barrel through the opening as the fraction-bound solid phase substrate is urged from the passageway in the barrel through the opening.

4. The method of claim 1 wherein the elusion buffer is immiscible with the isolation buffer and the biological sample.

5. A method for facilitating extraction of a fraction from a biological sample, the biological sample including non-desired material and a fraction-bound solid phase substrate, the method comprising the steps of:

positioning at least a portion of a plunger within a passageway extending along axis through a barrel of a syringe, the plunger being slidable along the axis and including:

an elongated stem having a first end received in the barrel; and a resilient plunger head extending radially from first end of the stem and terminating at a radially outer edge, the radially outer edge of the plunger head forming an airtight seal with an inner surface of the barrel;

sliding the plunger along the axis of the barrel in a first direction such that the plunger head is positioned adjacent an opening in a first end of the barrel;

positioning the opening in the first end of the barrel in fluid communication with an isolation buffer;

sliding the plunger along the axis of the barrel in a second direction, opposite to the first direction, for a first user-selected distance so as to draw the isolation buffer into the passageway in the barrel through the opening;

positioning the opening in the first end of the barrel in fluid communication with the biological sample;

sliding the plunger along the axis of the barrel in a second direction for a second user-selected distance, so as to draw the biological sample into the passageway in the barrel through the opening;

positioning a magnet adjacent to an outer surface of the barrel in proximity to the first end of the barrel such that a magnetic field generated by the magnet captures the fraction-bound solid phase substrate at a fixed location within the passageway through the barrel of the syringe;

sliding the plunger along the axis of the barrel in the first direction for a third distance to urge the biological sample and at least a portion of isolation buffer from the passageway in the barrel through the opening and the captured fraction-bound solid phase substrate are maintained in the passageway in the barrel at the fixed location;

removing the magnet from adjacent to an outer surface of the barrel such that the fraction-bound solid phase substrate is no longer captured at the fixed location within the passageway through the barrel of the syringe; and sliding the plunger along the axis of the barrel in the first direction such that the fraction-bound solid phase substrate is urged from the passageway in the barrel through the opening;

wherein prior to the step of positioning the opening in the first end of the barrel in fluid communication with the isolation buffer including the additional steps of:

positioning the opening in the first end of the barrel in fluid communication with an elusion buffer; and sliding the plunger along the axis of the barrel in the second direction for a third user-selected distance so as to draw the elusion buffer into the passageway in the barrel through the opening.

6. The method of claim 5 wherein prior to the step of removing the magnet from adjacent to the outer surface of the barrel, comprising the additional step of sliding the plunger along the axis of the barrel in the first direction such that at least a portion of the elusion buffer contacts the captured fraction-bound solid phase substrate at the fixed location.

7. The method of claim 5 wherein the elusion buffer is urged from the passageway in the barrel through the opening as the fraction-bound solid phase substrate is urged from the passageway in the barrel through the opening.

8. The method of claim 7 wherein the elusion buffer, the isolation buffer and the biological sample are immiscible.

9. A method for facilitating extraction of a fraction from a biological sample, the biological sample including non-desired material and a fraction-bound solid phase substrate, the method comprising the steps of:

positioning at least a portion of a plunger within a passageway extending along axis through a barrel of a syringe, the plunger being slidable along the axis and including:

an elongated stem having a first end received in the barrel; and a resilient plunger head extending radially from first end of the stem and terminating at a radially outer edge, the radially outer edge of the plunger head forming an airtight seal with an inner surface of the barrel;

sliding the plunger along the axis of the barrel in a first direction such that the plunger head is positioned adjacent an opening in a first end of the barrel;

positioning the opening in the first end of the barrel in fluid communication with an elusion buffer;

sliding the plunger along the axis of the barrel in a second direction, opposite to the first direction, for a first user-selected distance so as to draw the elusion buffer into the passageway in the barrel through the opening, positioning the opening in the first end of the barrel in fluid communication with an isolation buffer;

sliding the plunger along the axis of the barrel in the second direction for a second user-selected distance so as to draw the isolation buffer into the passageway in the barrel through the opening;

positioning the opening in the first end of the barrel in fluid communication with the biological sample;

sliding the plunger along the axis of the barrel in the second direction for a third user-selected distance, so as to draw the biological sample into the passageway in the barrel through the opening;

positioning a magnet adjacent to an outer surface of the barrel in proximity to the first end of the barrel such that a magnetic field generated by the magnet captures the fraction-bound solid phase substrate at a fixed location within the passageway through the barrel of the syringe;

sliding the plunger along the axis of the barrel in the first direction to urge the biological sample and the isolation buffer from the passageway in the barrel through the opening, wherein at least a portion of the elusion buffer and the captured fraction-bound solid phase substrate at the fixed location are maintained in the passageway in the barrel;

removing the magnet from adjacent to an outer surface of the barrel such that the fraction-bound solid phase substrate is no longer captured at the fixed location within the passageway through the barrel of the syringe; and sliding the plunger along the axis of the barrel in the first direction such that the at least the portion of the elusion buffer and fraction-bound solid phase substrate are urged from the passageway in the barrel through the opening into a vessel.

10. The method of claim 9 wherein the second end of the stem includes an enlarged head extending radially therefrom.

11. The method of claim 9 wherein the elusion buffer, the isolation buffer and the biological sample are immiscible.

12. The method of claim 9 comprising the additional step of operatively connecting the vessel to an additional downstream component for further processing of the fraction-bound solid phase substrate.

* * * * *